US007798969B2

(12) United States Patent
Hirayama et al.

(10) Patent No.: US 7,798,969 B2
(45) Date of Patent: Sep. 21, 2010

(54) ULTRASONIC PROBE

(75) Inventors: Michiyo Hirayama, Kanagawa (JP); Masahiro Shinkai, Tokyo (JP)

(73) Assignee: Panasonic Corporation, Osaka (JP)

( * ) Notice: Subject to any disclaimer, the term of this patent is extended or adjusted under 35 U.S.C. 154(b) by 483 days.

(21) Appl. No.: 10/598,198

(22) PCT Filed: Jul. 26, 2005

(86) PCT No.: PCT/JP2005/013664

§ 371 (c)(1),
(2), (4) Date: Aug. 21, 2006

(87) PCT Pub. No.: WO2006/011489

PCT Pub. Date: Feb. 2, 2006

(65) Prior Publication Data

US 2007/0167820 A1 Jul. 19, 2007

(30) Foreign Application Priority Data

Jul. 28, 2004 (JP) ............................ 2004-219476

(51) Int. Cl.
*A61B 8/14* (2006.01)

(52) U.S. Cl. ...................................... 600/459; 600/437

(58) Field of Classification Search ................. 600/459, 600/437, 444, 446, 447

See application file for complete search history.

(56) References Cited

U.S. PATENT DOCUMENTS 4,181,120 A * 1/1980 Kunii et al. ................. 600/459
5,460,179 A 10/1995 Okunuki et al.
2004/0254470 A1 * 12/2004 Drinkwater et al. ......... 600/459

FOREIGN PATENT DOCUMENTS

| | | |
|---|---|---|
| EP | 0 749 722 | 12/1996 |
| JP | 61-118307 | 7/1986 |
| JP | 1-42689 | 9/1989 |
| JP | 1-293850 | 11/1989 |
| JP | 5-57853 | 8/1993 |
| JP | 5-309092 | 11/1993 |
| JP | 2001-178727 | 7/2001 |

* cited by examiner

*Primary Examiner*—Long V Le
*Assistant Examiner*—Vani Gupta
(74) *Attorney, Agent, or Firm*—Hamre, Schumann, Mueller & Larson, P.C.

(57) ABSTRACT

In an ultrasonic probe including a storage portion formed with the coupling of a window and a frame for storing an ultrasonic device and an ultrasound propagation medium therein, the generation of a gap between the window and the frame due to a temperature change etc. can be suppressed. The ultrasonic probe includes an ultrasonic device (1) that transmits and receives ultrasound; a frame (4) that supports the ultrasonic device (1); a window (5) that is coupled with the frame (4) so as to surround the ultrasonic device (1); and an ultrasound propagation medium with which a space surrounded by the frame (4) and the window (5) is filled. The window (5) includes a resin portion (5*b*) having a property of letting ultrasound pass therethrough and a metal portion (5*a*), a part of the metal portion being embedded in an inside of the resin portion (5*b*) and another part being exposed to an outside of the resin portion (5*b*). The coupling of the window (5) and the frame (4) is implemented by coupling the part of the metal portion (5*a*) exposed to the outside of the resin portion (5*b*) with the frame (4).

12 Claims, 5 Drawing Sheets

FIG. 1A
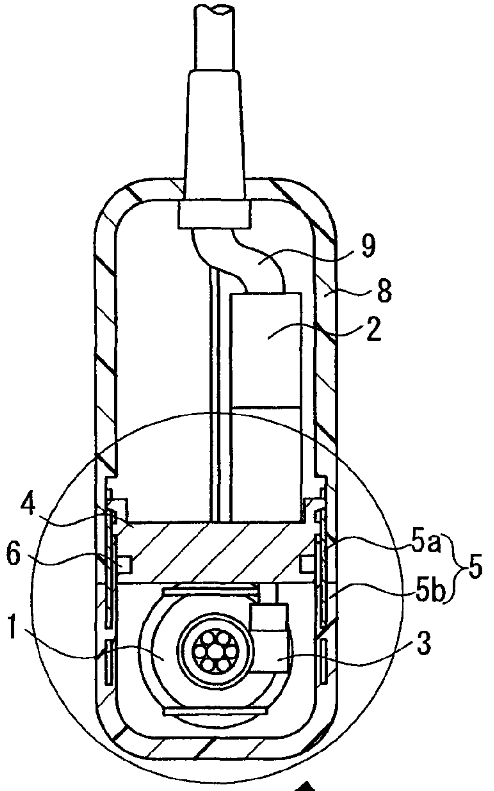
FIG. 1B
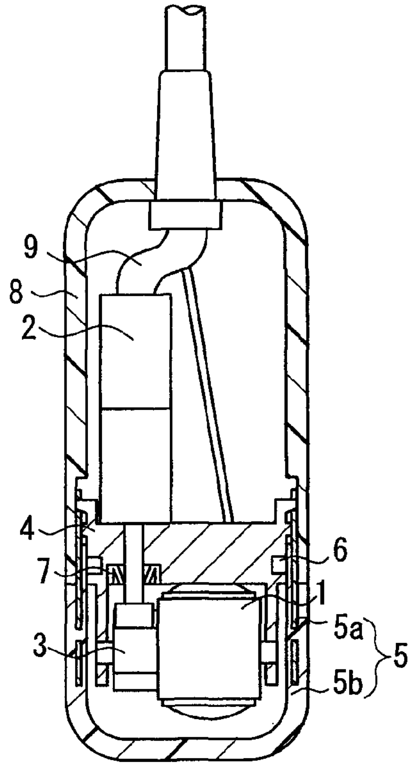
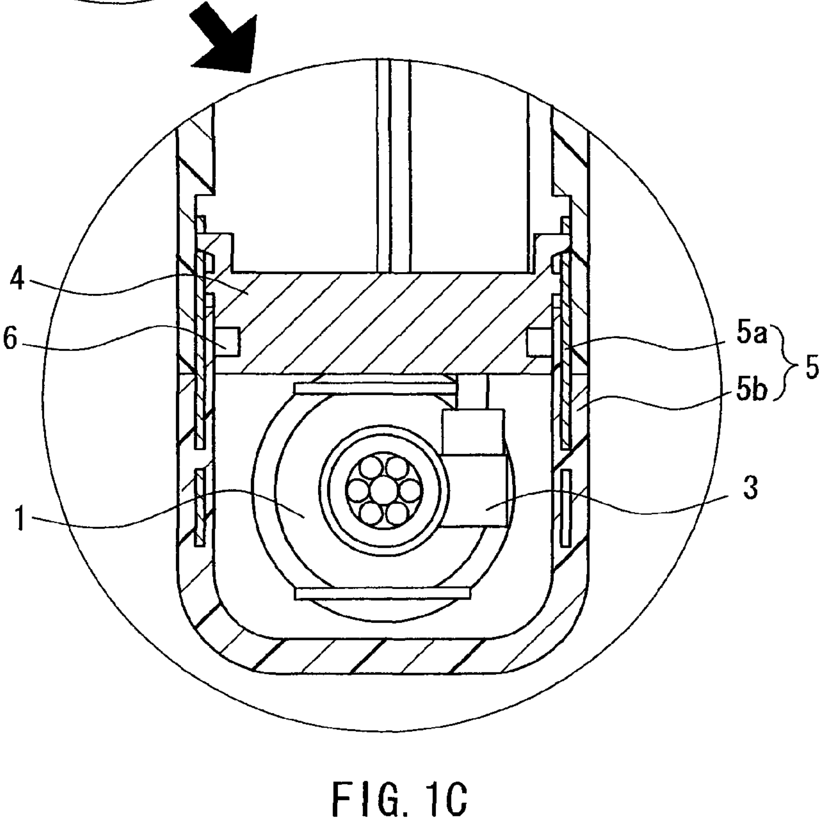
FIG. 1C

FIG. 3A
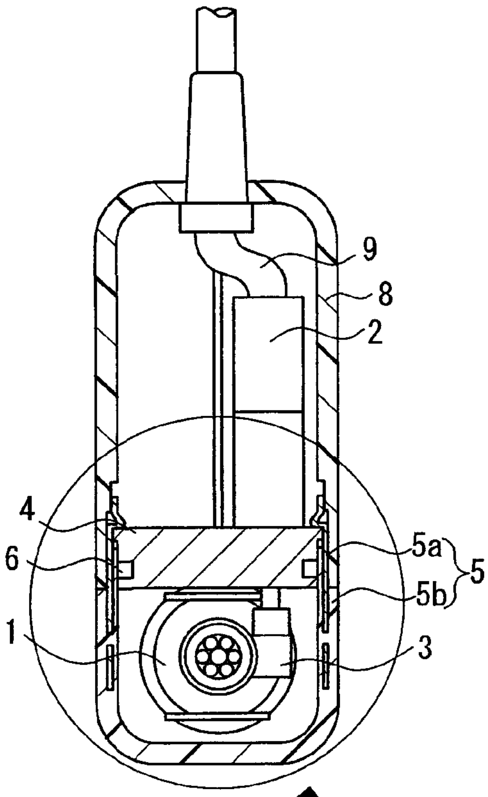
FIG. 3B
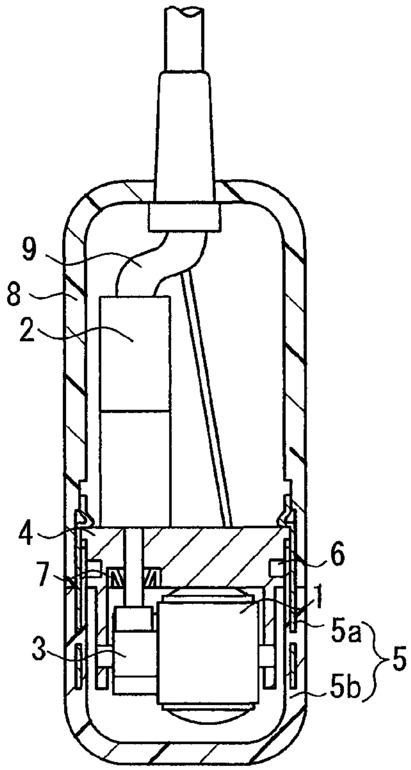
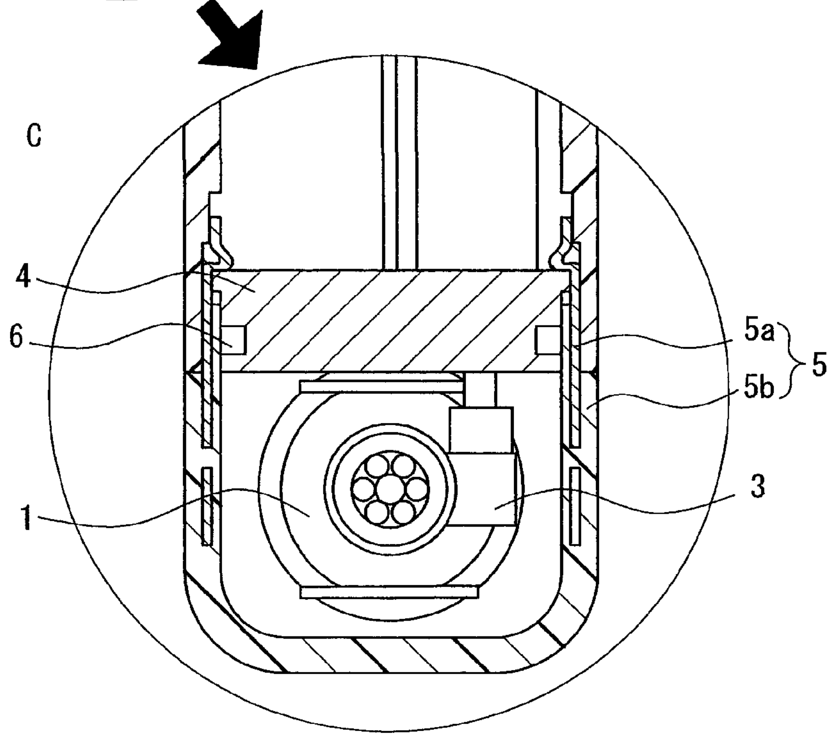
FIG. 3C

FIG. 4A
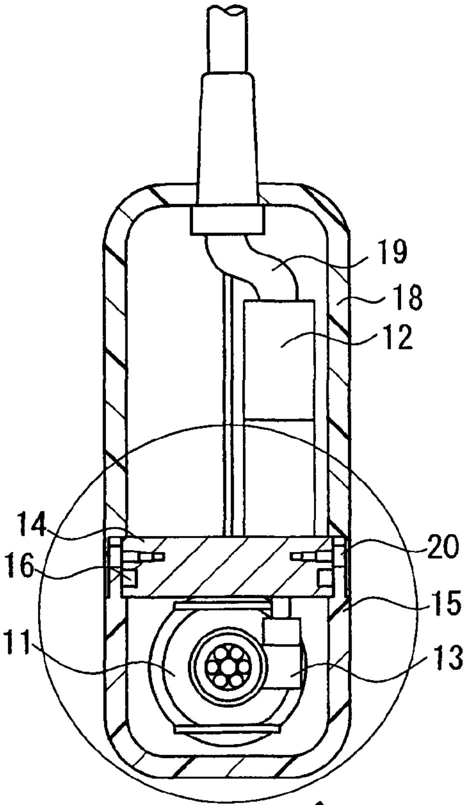
FIG. 4B
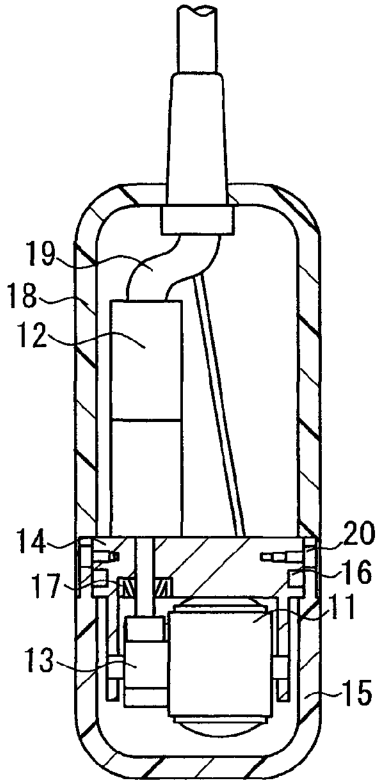
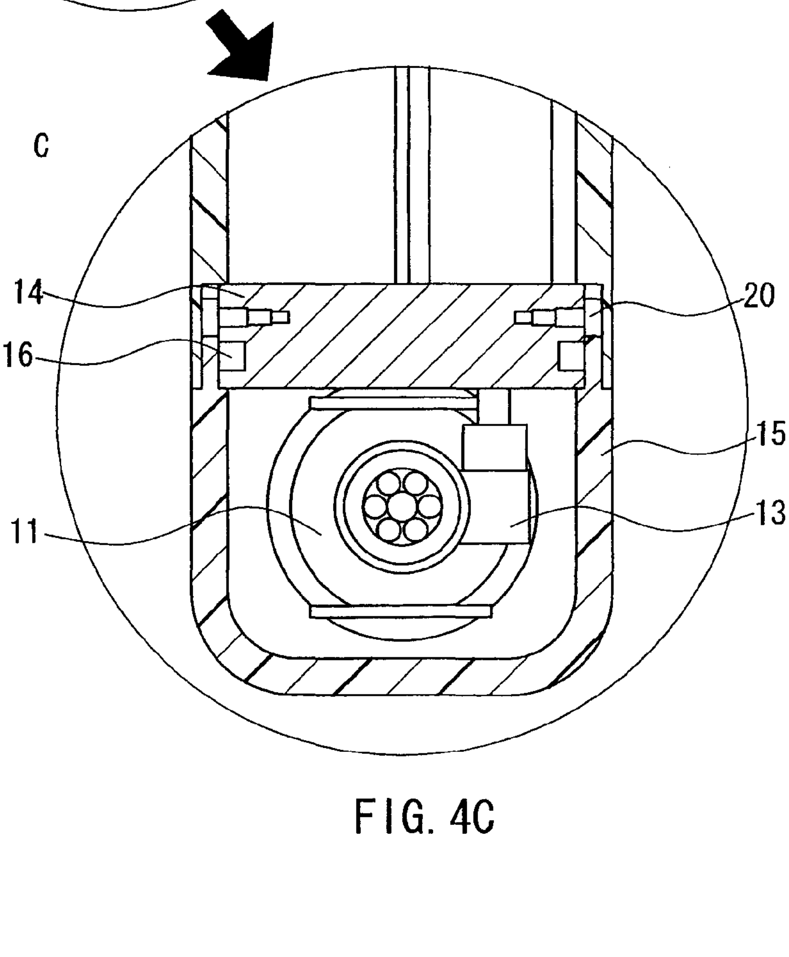
FIG. 4C

FIG. 5A
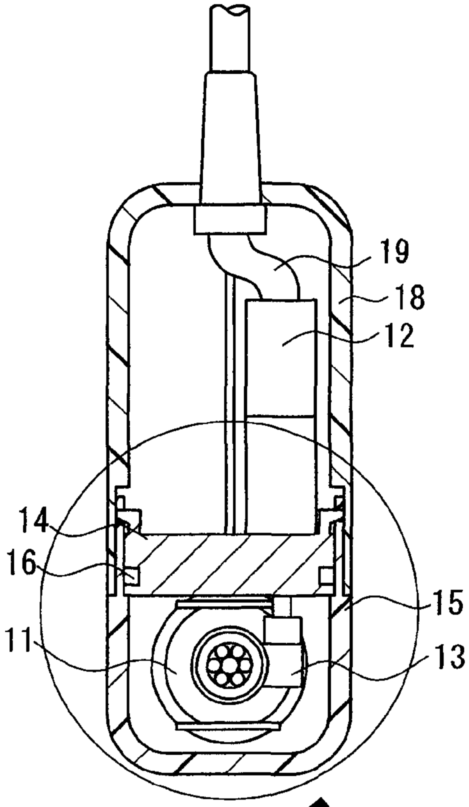
FIG. 5B
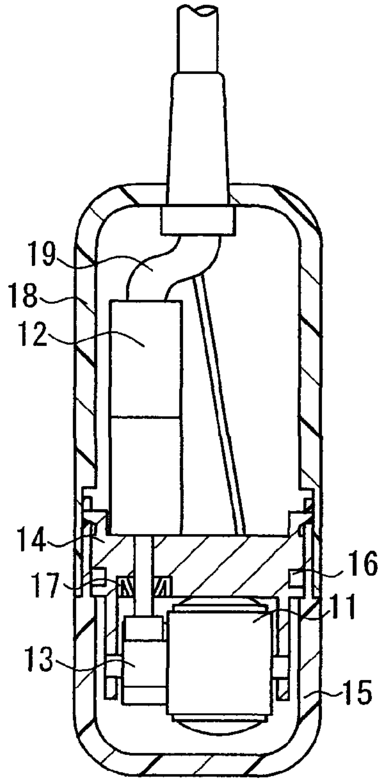
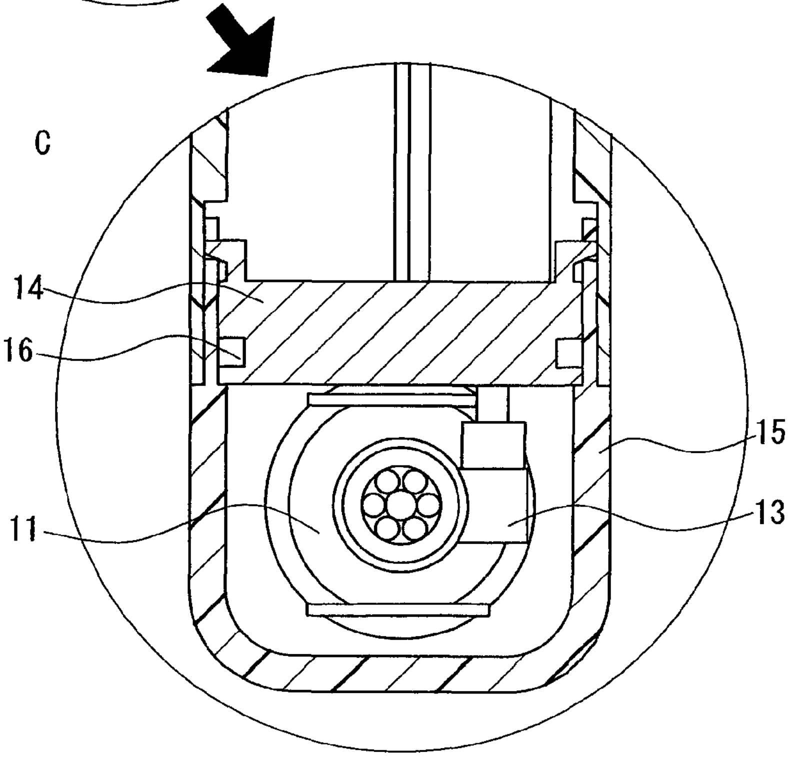
FIG. 5C

ULTRASONIC PROBE

TECHNICAL FIELD

The present invention relates to an ultrasonic probe that is used for ultrasonic diagnosis for medical use, for example.

BACKGROUND ART

A known ultrasonic probe for use in ultrasonic diagnostic apparatuses includes an ultrasonic device that is rotated or swung in a storage portion filled with an ultrasound propagation medium having an acoustic impedance close to that of a living body, thereby transmitting and receiving ultrasound.

FIGS. 4 and 5 show the configurations of such a conventional ultrasonic probe in cross section. In these ultrasonic probes, a window 15 and a frame 14 are coupled so as to constitute the storage portion, which is filled with an ultrasound propagation medium (not illustrated). The boundary between the window 15 and the frame 14 is provided with an O-ring 16 for preventing the leakage of the medium. In this storage portion, an ultrasonic device 11 and a driving transmission portion 13 are disposed. The driving transmission portion 13, connected with an output shaft of a driving portion 12 disposed outside of the storage portion, is configured so as to transmit the power of the driving portion 12 to the ultrasonic device so as to enable the rotational movement of the ultrasonic device. In FIGS. 4 and 5, reference numeral 18 denotes a housing for storing the driving portion 12 and the like therein, 19 denotes a cable for the connection between the probe and an external apparatus (e.g., an ultrasonic diagnosis apparatus), and 17 denotes an oil seal.

In the above-stated ultrasonic probe, the window generally is made of a resin having an acoustic impedance close to that of a living body. The frame generally is made of a metal because of the excellent stability of the shape. The window and the frame are coupled by means of the securing with a screw 20 as well as the bonding with an adhesive as shown in FIG. 4, or by means of the bonding with an adhesive as shown in FIG. 5.

Patent document 1: JP H01(1989)-42689 A

DISCLOSURE OF INVENTION

Problem to be Solved by the Invention

In the above-stated conventional ultrasonic probes, however, there is a significant difference in coefficient of thermal expansion or rigidity between the resin constituting the window 15 and the metal constituting the frame 14. Therefore, when the temperature changes or an external shock is applied mechanically, a gap may be generated at the coupling portion of the window and the frame, thus causing the leakage of the ultrasound propagation medium from the storage portion or the intrusion of bubbles therein. Particularly, in the case of the intrusion of bubbles into the storage portion, the bubbles will function as a reflection body for the ultrasound, thus causing the problem of impeding the transmission/reception of ultrasound.

Further, in the above-stated conventional ultrasonic probes, in order to prevent the generation of a gap between the window 15 and the frame 14, an adhesive is applied at an interface of the both members. However, since the resin constituting the window 15, particularly, polymethyl pentene has a poor adhesiveness, there is a problem of a tendency to degrade the liquid seal effect.

In order to cope with the above-stated problems, it is an object of the present invention to suppress the generation of a gap between the window and the frame when the temperature changes or the like, so as to provide an ultrasonic probe with excellent reliability.

Means for Solving Problem

In order to achieve the above-stated object, the ultrasonic probe of the present invention includes: an ultrasonic device that transmits and receives ultrasound; a frame that supports the ultrasonic device; a window that is coupled with the frame so as to surround the ultrasonic device; and an ultrasound propagation medium with which a space surrounded by the frame and the window is filled. The window includes a resin portion having a property of letting ultrasound pass therethrough and a metal portion, a part of the metal portion being embedded in an inside of the resin portion and another part being exposed to an outside of the resin portion. The coupling of the window and the frame is implemented by coupling the part of the metal portion exposed to the outside of the resin portion with the frame.

Effects of the Invention

According to the above-stated ultrasonic probe of the present invention, the coupling of the window and the frame is implemented by coupling the metal portion provided in the window with the frame. Therefore, a difference in coefficient of thermal expansion between the both members at their coupling portion can be made relatively small, so that stable coupling can be achieved even when a temperature changes. Further, the metal portion of the window is provided so that a part thereof is embedded in the inside of the resin portion. Therefore, the coupling of the metal portion and the resin portion of the window can be made relatively stable. As a result, according to the present invention, even when a temperature changes, the generation of a gap between the window and the frame and the leakage of the acoustic propagation medium and the intrusion of bubbles caused by the gap generated can be suppressed, and therefore the ultrasonic probe can have excellent reliability.

BRIEF DESCRIPTION OF DRAWINGS

FIG. 1 shows an exemplary ultrasonic probe according to the present invention in cross section (FIGS. 1A and B) and in partially enlarged view (FIG. 1C).

FIG. 2 shows an exemplary window constituting the above-stated ultrasonic probe, where

FIG. 3 shows another exemplary ultrasonic probe according to the present invention, where FIGS. 3A and B are cross-sectional views and FIG. 3C is a partially enlarged view of FIGS. 3A and B.

FIG. 4 shows a conventional ultrasonic probe, where FIGS. 4A and B are cross-sectional views and FIG. 4C is a partially enlarged view of FIGS. 4A and B.

FIG. 5 shows another conventional ultrasonic probe, where FIGS. 5A and B are cross-sectional views and FIG. 5C is a partially enlarged view of FIGS. 5A and B.

DESCRIPTION OF THE INVENTION

Figure 2A:
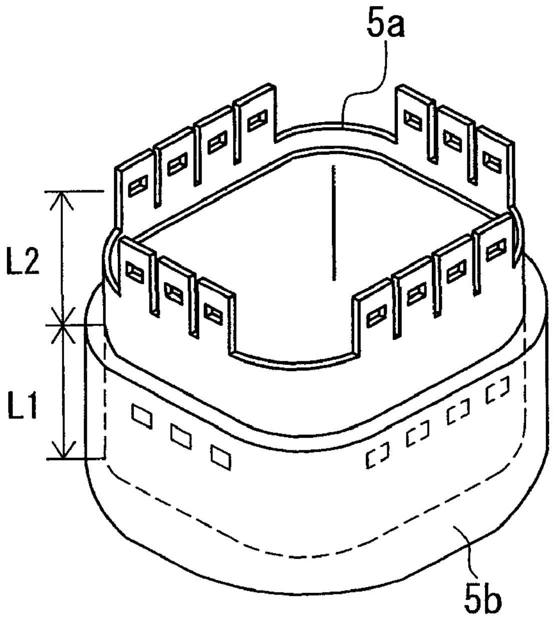
FIG. 2A is a perspective view and FIG. 2B is an exploded view.

As described above, according to the configuration of the present invention, even when a temperature changes, the generation of a gap between the window and the frame and the leakage of the acoustic propagation medium and the intrusion of bubbles caused by the gap generated can be suppressed, and therefore the ultrasonic probe can have excellent reliability.

In the above-stated ultrasonic probe, the metal portion of the window at the part embedded in the inside of the resin portion preferably is not in a simple flat plate shape but has a through hole, a convexo-concave structure, a part subjected to a surface-roughening treatment, a bending part or the like. With such a preferable example, the coupling of the metal portion and the resin portion can be reinforced further, thus suppressing the displacement and disengagement of the metal portion and the like.

In the above-stated ultrasonic probe, the window preferably is manufactured by insert molding. With such a preferable example, the coupling of the metal portion and the resin portion can be reinforced further, thus suppressing the displacement and disengagement of the metal portion and the like.

In the above-stated ultrasonic probe, the window and the frame preferably are coupled without an adhesive. In the case where an adhesive is not used, the problem of the adhesive flowing to an undesired location, resulting in degradation of the liquid seal effect, can be avoided.

As an example of such a coupling configuration, a male-shaped part or a female-shaped part may be provided at each of coupling faces of the frame and the part of the metal portion exposed to the outside of the resin portion, and the male-shaped part and the female-shaped part may be engaged so as to couple the metal portion and the frame. As another example, a hook may be provided at the part of the metal portion exposed to the outside of the resin portion, and the metal portion and the frame may be coupled by latching with the hook.

In the above-stated ultrasonic probe, the metal portion preferably is disposed so as to surround at least a part of the ultrasonic device other than an ultrasound transmission/reception face of the ultrasonic device. It is desired that the ultrasonic probe, at least the ultrasonic device thereof, be shielded electrically so as not to influence other medical equipment electrically and so as to be free from external electrical influences. With such a preferable example, the metal portion of the window can be used as such a shielding member.

The following is a detailed description of embodiments of the present invention, with reference to the drawings.

FIG. 1 shows an exemplary ultrasonic probe according to the present invention. This ultrasonic probe is of a mechanically scanning type ultrasonic probe that implements the scanning of an ultrasonic beam by rotating an ultrasonic device mechanically. FIGS. 1A and B are cross-sectional views that are cut along the directions mutually intersecting at right angles. FIG. 1C is a partially enlarged view of FIG. 1A.

In this ultrasonic probe, a window 5 is coupled with a frame 4 so as to constitute a storage portion. The window 5 and the frame 4 are described later in detail.

An ultrasonic device 1 is disposed in the storage portion. The ultrasonic device 1 includes an oscillator for transmitting/receiving ultrasound and a rotor for holding this oscillator. The rotor is supported rotatably by a bracket secured to or integrally formed with the frame 4. Further, a driving transmission portion 3 is connected with the rotor. A driving portion 2 further is disposed outside of the storage portion. This driving portion 2 is secured to the frame 4, and an output shaft of the driving portion 2 is connected to the driving transmission portion 3 in the storage portion via a through hole provided in the frame 4. With this configuration, the driving force from the driving portion 2 can be transmitted to the rotor via the driving transmission portion 3 so as to rotate the rotor, and in connection with this rotation, the oscillator is rotated, whereby ultrasound can be scanned mechanically along a circular path.

Further, the storage portion is filled with an ultrasound propagation medium (not illustrated) for transmitting ultrasound. At the boundary between the window 5 and the frame 4 is provided with an O-ring 6 for preventing the leakage of the ultrasound propagation medium. Further, at the boundary between the output shaft of the driving portion 2 and the frame 4 is provided with an oil seal 7 for preventing the leakage of the ultrasound propagation medium.

The frame 4 and the driving portion 2 are surrounded with a housing 8, through which a cable 9 is led out. This cable 9 allows the connection of the ultrasonic probe with an external apparatus such as an ultrasonic diagnosis apparatus during operation.

The following describes an operation of the above-stated ultrasonic probe. During operation, the ultrasonic probe is connected with an ultrasonic diagnosis apparatus. For the ultrasonic diagnosis, firstly, the ultrasonic probe is placed on a surface of a living body as a subject. At this time, the window 5 directly contacts with the living body or indirectly contacts via an ultrasound propagation medium. Then, the driving portion 2 of the probe is activated by a driving signal from the ultrasonic diagnosis apparatus, so as to rotate the ultrasonic device 1. Subsequently, an electric signal (transmission signal) is transmitted from the ultrasonic diagnosis apparatus to the ultrasonic probe. The transmission signal is converted to ultrasound by the ultrasound device of the probe so as to propagate through the ultrasound propagation medium, pass through the window 5 and arrive at the living body. This ultrasound is reflected from a target within the living body, and a part of the reflected wave is received by the ultrasonic device 1 of the probe, which then is converted to an electric signal (reception signal) and is transmitted to the ultrasonic diagnosis apparatus. This transmission/reception operation is performed repeatedly while rotating the ultrasonic device 1, whereby the ultrasound scanning is enabled. The ultrasonic diagnosis apparatus creates an ultrasonic image of the target based on the reception signal (e.g., a tomogram) and displays the image.

The following is a further detailed description of the window 5 and the frame 4 constituting the above-stated ultrasonic probe.

In the above-stated ultrasonic probe, the window 5 is provided with a resin portion 5*b* and a metal portion 5*a* as shown in FIG. 1C. The window 5 is configured so that the resin portion 5*b* is disposed at least at a portion serving as a propagation path of ultrasound and the metal portion 5*a* is disposed at least at a portion serving as the coupling portion with the frame 4. Further, as described above, the metal portion 5*a* preferably is disposed so as to surround at least a part of the ultrasound device other than the transmission/reception face of ultrasound (i.e., the side faces of the ultrasonic device).

The material constituting the resin portion 5*b* is not limited especially as long as it allows ultrasound to pass through, and a material having an acoustic impedance close to that of a subject body (e.g., a living body) preferably is used. Such a material includes polymethyl pentene, for example. The material constituting the metal portion 5*a* is not limited especially, and a stainless steel can be used, for example.

Figure 2B:
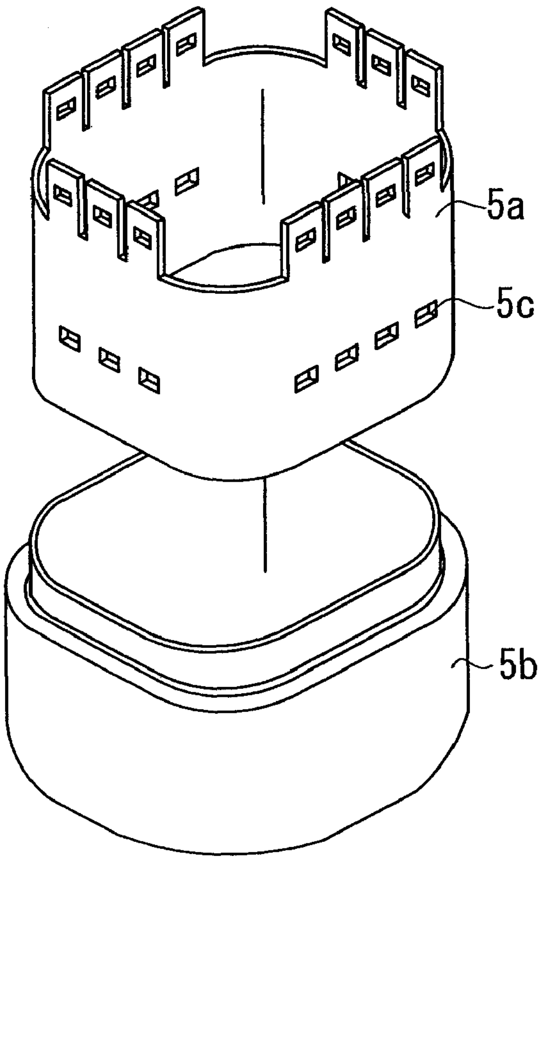

FIG. 2 shows an exemplary configuration of the window 5, where FIG. 2A is a perspective view and FIG. 2B is an exploded view. As shown in these drawings, a part (L1 part) of the metal portion 5*a* is embedded inside the resin portion 5*b* and another part (L2 part) is exposed to the outside of the resin portion 5*b*.

The part of the metal portion 5*a* embedded inside the resin portion 5*b* preferably has a part in a specific shape and not in a simple flat plate shape, which is for increasing the coupling force with the resin portion 5*b*.

As an exemplary configuration of such a metal portion 5*a*, through holes (e.g., apertures 5*c*) may be provided in the part of the metal portion 5*a* embedded inside the resin portion 5*b* as shown in FIG. 2. In such a configuration, the resin constituting the resin portion 5*b* is allowed to get into the apertures 5*c* of the metal portion 5*a*, so that the resin 5*b* can be made integral with the periphery of the metal portion 5*a* through the apertures 5*c*, and therefore the coupling force between the metal portion 5*a* and the resin portion 5*b* can be increased. The shape and the dimensions of the through holes are not limited especially, but if they are too small, it may be difficult for a resin to get into the apertures, depending on the resin viscosity. Therefore, the through holes preferably have an aperture dimension of 1 mm or more at least partially in view of the viscosity of the resin and the strength after molding. The method for forming the through holes is not limited especially, and they can be formed by stamping processing, for example.

As another configuration, concaves, convexes or both of them may be provided at a surface of the metal portion 5*a*. The shape of the convexo-concave structure is not limited especially, and for instance the shape including a plurality of convexes aligned like discrete islands, the shape including a plurality of concaves aligned like grooves or the like is available. Such a convexo-concave structure can be formed by emboss processing, knurl processing, etching, half-punching and the like.

As still another configuration, a surface-roughening treatment may be applied to the surface of the metal portion 5*a* at a part embedded inside the resin portion 5*b*. As the surface-roughening treatment, a chemical treatment and a physical treatment both can be used. As the chemical treatment, for instance, the metal portion may be immersed in an aqueous solution of iron chloride, copper chloride or the like so as to etch the surface of the metal portion. As the physical treatment, for instance, powder made of aluminum oxide or the like may be blown to the surface of the metal portion together with compressed air.

Further, the metal portion 5*a* may be bent partially at the part embedded inside the resin portion 5*b* (preferably, at the end portion located at the deepest portion of the resin portion 5*b*). In this case, the bending angle of the metal portion 5*a* preferably is set at 90° or more.

Such a window 5 provided with the metal portion 5*a* and the resin portion 5*b* can be manufactured by insert molding. That is, the metal portion 5*a* to be inserted is charged at a predetermined position of a die, followed by filling this die with a resin material constituting the resin portion 5*b*, and the molten resin is solidified while surrounding a part of the metal portion 5*a* with the molten resin. Thereby, the window 5 in which the metal portion 5*b* and the resin portion 5*b* further are combined can be manufactured.

Meanwhile, in the above-stated ultrasonic probe, the frame 4 is a member that supports the ultrasonic device and is coupled with the window so as to constitute the storage portion as described above. As the material thereof, a metal may be used because of the excellent stability of the shape. The metal is not limited especially and aluminum preferably is used because it is lightweight and has excellent processability.

The coupling of the window 5 and the frame 4 is implemented by the coupling of the metal portion 5*a* of the window with the frame 4, as described above.

As an exemplary coupling method, a male/female configuration may be formed at the respective coupling faces of the frame 4 and the part of the metal portion 5*a* exposed to the outside of the resin portion 5*b*, and the male and female shapes may be engaged for coupling. More specifically, as shown in FIG. 1, a through hole may be provided in the metal portion 5*a* at a part to be coupled with the frame 4 (i.e., at a part that is exposed to the outside of the resin portion 5*b*), and a convex in a shape allowing the engagement with the through hole is provided in the frame 4 at a part to be coupled with the metal portion 5*a*, and the through hole and the convex may be engaged. Conversely, a convex may be provided in the metal portion 5*a* at a part to be coupled with the frame 4 and a through hole in a shape allowing the engagement with the convex may be provided in the frame 4 at a part to be coupled with the metal portion 5*a*, and they may be engaged. Instead of the through hole, a concave in a shape allowing the engagement with the convex may be used.

FIG. 3 shows another exemplary coupling way for the window 5 and the frame 4 in cross section. In this drawing, the same reference numerals are assigned to the same members as those in FIG. 1. In this configuration, a hook is formed at a part of the metal portion 5*a* exposed to the outside of the resin portion 5*b*, and this hook contacts with the end face of the frame 4 so as to hold the same. With this configuration, the hook provided at the metal portion 5*a* latches the frame, whereby the metal portion 5*a* and the frame 4 can be coupled.

In any configuration, the window and the frame can be coupled without the use of an adhesive. In the case where an adhesive is not used, the problem of the adhesive attached to the sealing surface of the O-ring 6, thus degrading the liquid seal effect can be avoided. Further, there is another advantage of facilitating the disassembling of the product without destruction of the product.

In the above-stated ultrasonic probe, as described above, the window and the frame can be coupled by coupling the metal portion provided in the window with the frame. As one example, the following shows coefficients of linear expansion of typical materials constituting the resin portion and the metal portion of the window and the frame:

Window resin portion (polymethyl pentene)=$1.17\times10^{-4}$ mm/mm·° C.

Window metal portion (stainless steel)=$0.18\times10^{-4}$ mm/mm·° C.

Frame (aluminum)=$0.24\times10^{-4}$ mm/mm·° C.

In this way, in the above-stated ultrasonic probe, a difference in coefficient of thermal expansion between the members constituting the window and the frame at their coupling portion can be made relatively small. As a result, the coupling of the window and the frame can be made relatively stable irrespective of a temperature change, and therefore an ultrasonic probe with excellent reliability can be provided.

INDUSTRIAL APPLICABILITY

As described above, according to the ultrasonic probe of the present invention, even when a temperature changes, the generation of a gap between the window and the frame and the leakage of the acoustic propagation medium and the intrusion of bubbles caused by the gap generated can be suppressed, and therefore the ultrasonic probe is excellent in reliability. Thus, the ultrasonic probe is effective for use in an ultrasonic diagnosis apparatus or the like.

The invention claimed is:

1. An ultrasonic probe, comprising:

an ultrasonic device that transmits and receives ultrasound;

a frame that supports the ultrasonic device;

a window that is coupled with the frame so as to surround the ultrasonic device; and an ultrasound propagation medium with which a space surrounded by the frame and the window is filled, wherein the ultrasonic device is a accommodated in a space that is surrounded by the frame and the window and that is filled with the ultrasound propagation medium, the window comprises a resin portion having a property of letting ultrasound pass therethrough and a metal portion, a part of the metal portion being embedded in an inside of the resin portion and another part not being covered with the resin portion at a position opposed to a peripheral portion of the frame, and wherein the window and the frame are coupled by directly coupling the part of the metal portion that is not covered with the resin portion with the frame.

2. The ultrasonic probe according to claim 1, wherein a through hole is provided in the metal portion at the part embedded in the inside of the resin portion.

3. The ultrasonic probe according to claim 1, wherein a convexo-concave structure is provided at the metal portion at the part embedded in the inside of the resin portion.

4. The ultrasonic probe according to claim 1, wherein a surface-roughening treatment is applied to the metal portion at the part embedded in the inside of the resin portion.

5. The ultrasonic probe according to claim 1, wherein a bending portion is provided at the metal portion at the part embedded in the inside of the resin portion.

6. The ultrasonic probe according to claim 1, wherein the window is manufactured by insert molding.

7. The ultrasonic probe according to claim 1, wherein a male-shaped part and a female-shaped part are provided at coupling faces of the frame and the part of the metal portion exposed to the outside of the resin portion, and the male-shaped part and the female-shaped part are engaged so as to couple the metal portion and the frame.

8. The ultrasonic probe according to claim 1, wherein a hook is provided at the part of the metal portion exposed to the outside of the resin portion, and the metal portion and the frame are coupled by latching with the hook.

9. The ultrasonic probe according to claim 1, wherein the metal portion is disposed so as to surround at least a part of the ultrasonic device other than an ultrasound transmission/reception face of the ultrasonic device.

10. The ultrasonic probe according to claim 1, wherein the resin portion is made of polymethyl pentene.

11. The ultrasonic probe according to claim 1, wherein the metal portion is made of stainless steel.

12. The ultrasonic probe according to claim 1, wherein the frame is made of metal.

* * * * *